United States Patent
Doi et al.

(10) Patent No.: US 7,381,951 B2
(45) Date of Patent: Jun. 3, 2008

(54) CHARGED PARTICLE BEAM ADJUSTMENT METHOD AND APPARATUS

(75) Inventors: Takashi Doi, Hitachinaka (JP); Noriaki Arai, Hitachinaka (JP); Hidetoshi Morokuma, Hitachinaka (JP); Katsumi Setoguchi, Hitachinaka (JP); Fumihiro Sasajima, Hitachinaka (JP); Maki Tanaka, Yokohama (JP); Atsushi Miyamoto, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/209,759

(22) Filed: Aug. 24, 2005

(65) Prior Publication Data

US 2006/0043293 A1 Mar. 2, 2006

(30) Foreign Application Priority Data

Aug. 30, 2004 (JP) ............................. 2004-249434

(51) Int. Cl.
*G21K 7/00* (2006.01)
(52) U.S. Cl. ............ 250/310; 250/396 R; 250/396 ML
(58) Field of Classification Search ................ 250/310, 250/396 R, 396 ML
See application file for complete search history.

(56) References Cited

U.S. PATENT DOCUMENTS

| 6,452,175 B1 | 9/2002 | Adamec et al. |
| 6,570,156 B1 * | 5/2003 | Tsuneta et al. ............. 250/311 |
| 6,614,026 B1 | 9/2003 | Adamec et al. |
| 6,956,211 B2 | 10/2005 | Sato et al. |

FOREIGN PATENT DOCUMENTS

| JP | 55-48610 | 3/1980 |
| JP | 2-33843 | 2/1990 |

* cited by examiner

*Primary Examiner*—David Vanore
(74) *Attorney, Agent, or Firm*—Dickstein Shapiro LLP

(57) ABSTRACT

A charged particle beam adjustment apparatus for tilting an electron beam by a tilt deflector is disclosed. The tilt angle adjustment of the electron beam and the distortion adjustment for correcting the image distortion generated when the electron beam is tilted are conducted on a specified. sample such as a pyramidal sample. The images before and after the tilting are acquired and processed to determine the tilt angle value and the distortion amount. The tilt angle adjustment and the adjustment for correction of the distortion are automated in accordance with a predetermined processing flow.

9 Claims, 7 Drawing Sheets

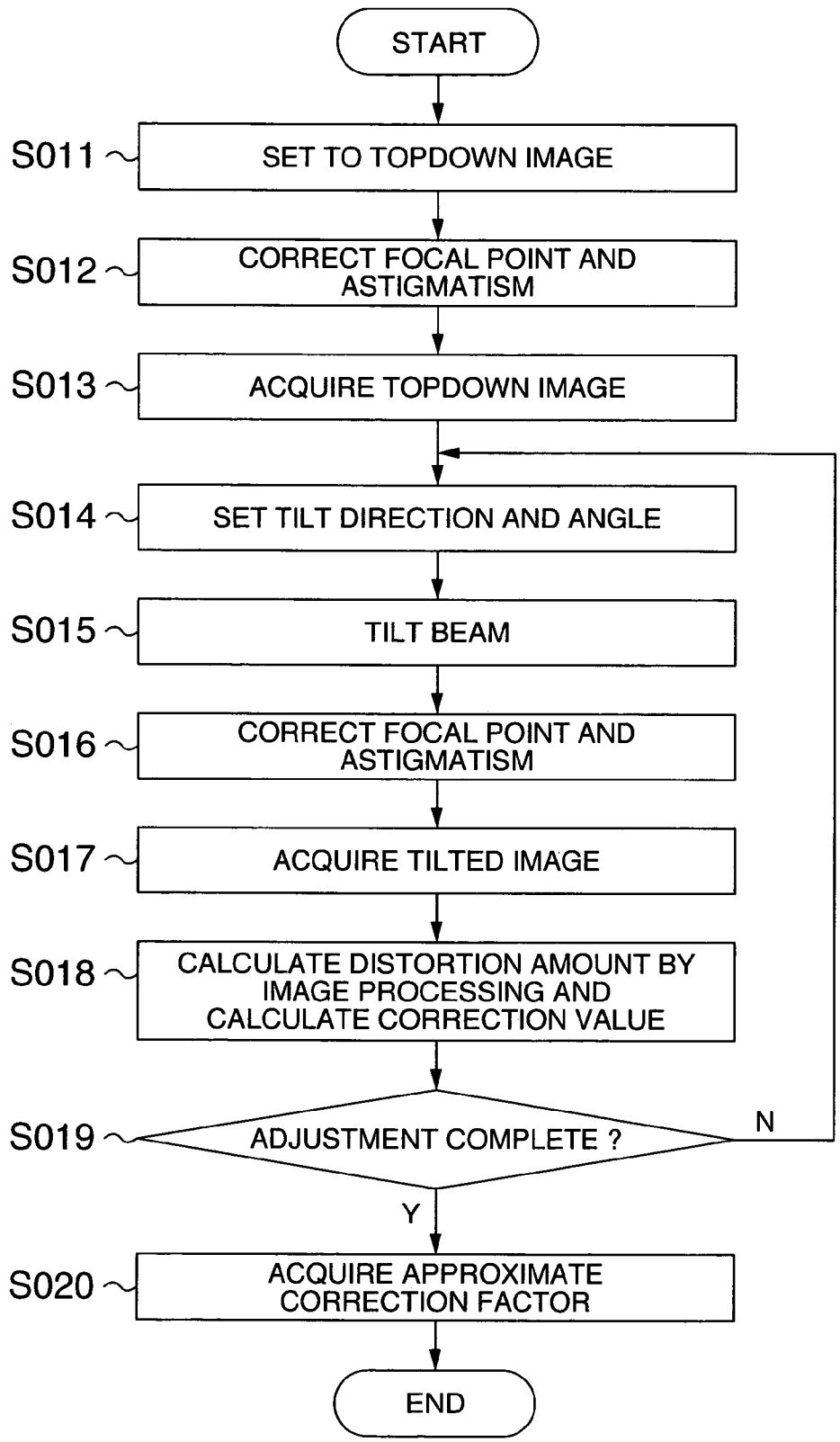

FIG. 4A
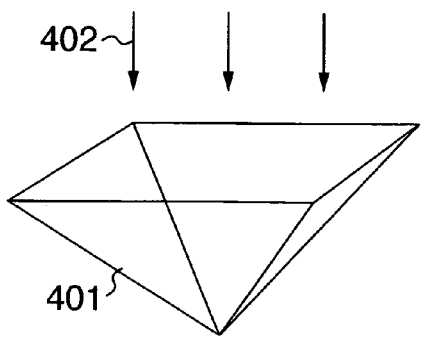
FIG. 4B
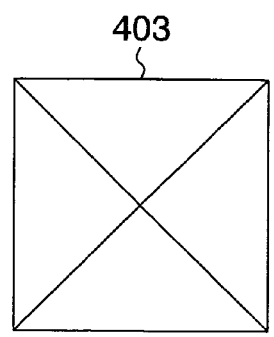
FIG. 4C
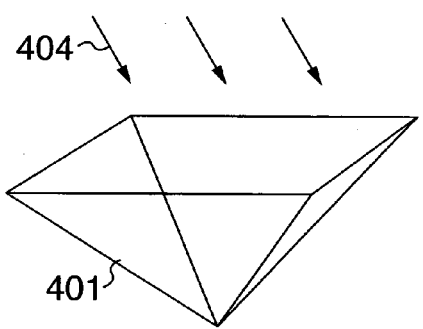
FIG. 4D
FIG. 4E
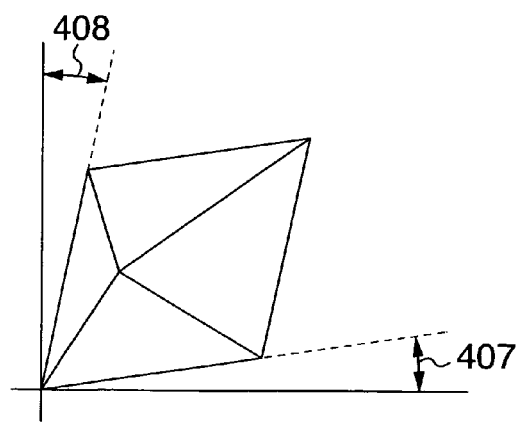
FIG. 4F
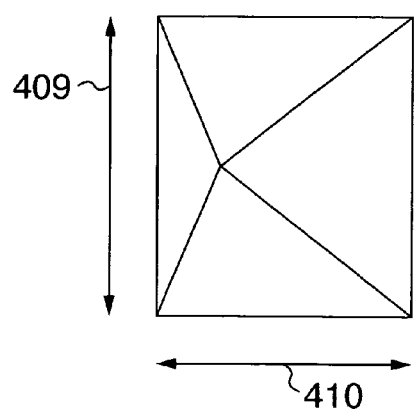

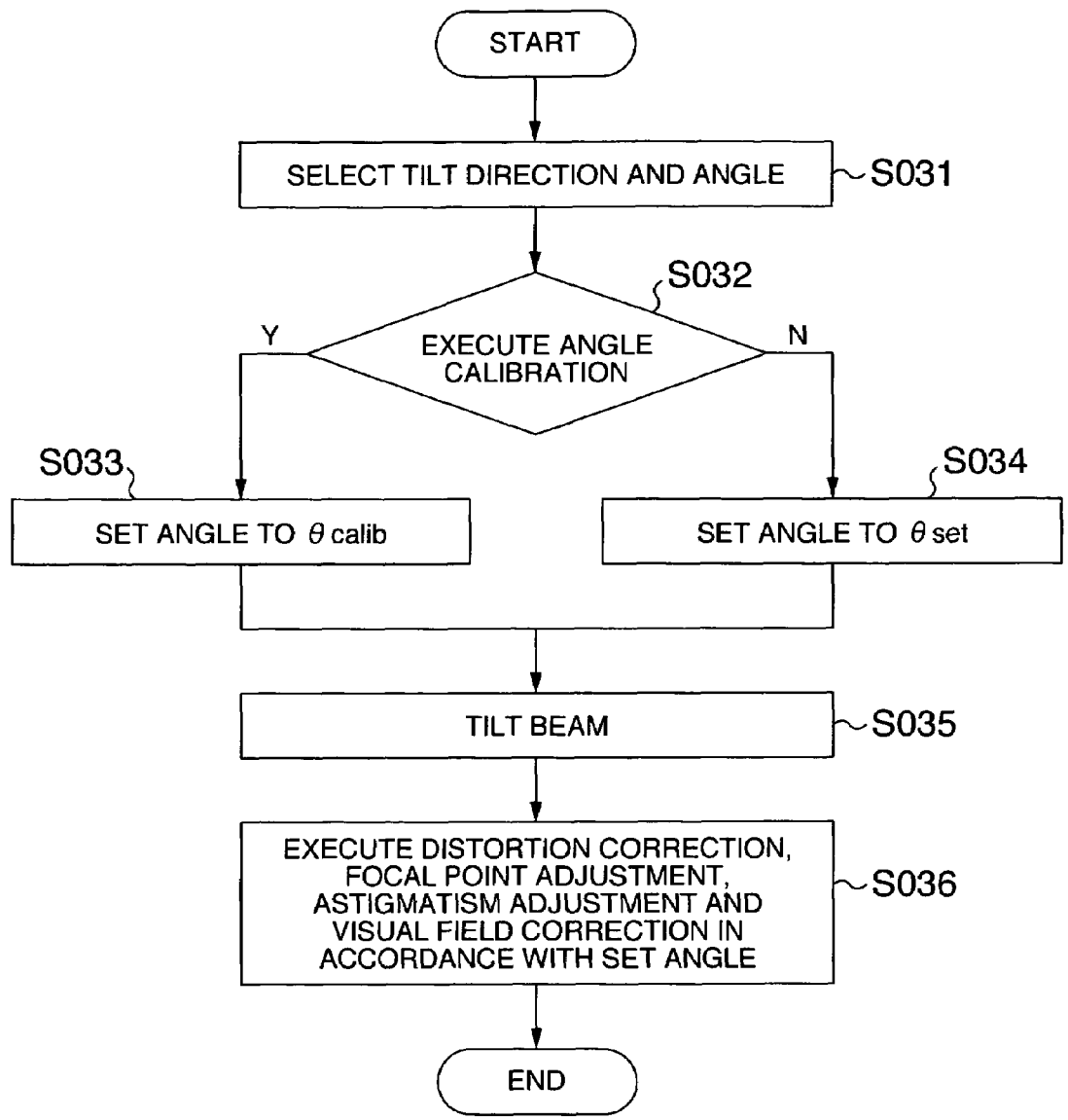

CHARGED PARTICLE BEAM ADJUSTMENT METHOD AND APPARATUS

BACKGROUND OF THE INVENTION

This invention relates to a method for adjusting the beam conditions of the charged particle beam and a charged particle beam apparatus, or in particular to a charged particle beam adjustment method for adjusting the angle and distortion and calibrating the angle of a tilted beam and a charged particle beam apparatus.

In the charged particle beam apparatus of which a typical example is the scanning electron microscope (SEM), a thinly focused charged particle beam is scanned on a sample to obtain the desired information such as a sample image from the sample. The resolution of this charged particle beam apparatus has been improved every year. At the same time, it has recently come to be considered necessary to obtain a tilted image of the sample by tilting the charged particle beam with respect to the sample. To obtain a tilted image of a sample, it is common practice to tilt a sample stage. For preventing the shift of the visual field at high magnification or obtaining a tilted image of a sample at high speed, however, it is more reasonable to tilt the charged particle beam with respect to the sample rather than to tilt the sample stage mechanically.

JP-A-55-48610 (U.M.) and JP-A-2-33843, for example, disclose a technique for radiating a tilted beam, in which the charged particle beam is incident out of axis of an objective lens and the beam is tilted utilizing the focusing action or the restoration action of the objective lens.

The conventional techniques described above, however, refer to nothing about a method of angle adjustment of a tilted beam, a method of automating the adjustment, a method of correcting the image distortion at the time of tilting the beam or a method of automatic adjustment thereof. In order to tilt the beam accurately, it is necessary to correct the tilt angle and the image distortion at the time of tilting the beam for each direction. Also, the adjustment is required to be easy and efficient.

SUMMARY OF THE INVENTION

The object of this invention is to provide a beam condition adjustment method suitable for adjusting the conditions for a beam different from those for a vertical beam, and an apparatus using the method.

In order to achieve the object described above, according to an embodiment of the invention, there is provided a charged particle beam apparatus for tilting the beam using a tilt deflector, wherein the beam tilt angle adjustment and the distortion adjustment for correcting the image distortion at the time of tilting an electron beam are carried out using a specific sample such as a pyramidal sample, and wherein the tilt angle value and the distortion amount are determined by processing the images acquired before and after the tilt, and the the tilt angle adjustment and the adjustment for correcting the image distortion are automated in accordance with a predetermined processing flow.

According to this invention, there is provided a beam condition adjustment method suitable for adjusting the beam conditions at the time of tilting a beam and an apparatus using the method.

Other objects, features and advantages of the invention will become apparent from the following description of the embodiments of the invention taken in conjunction with the accompanying drawings.

BRIEF DESCRIPTION OF THE DRAWINGS

FIG. 3 is a flowchart for explaining the distortion adjustment method at the time of tilting an electron beam.

FIGS. 4A-4F are schematic diagrams showing examples of image distortion at the time of tilting an electron beam.

FIG. 7 is a flowchart for reflecting the result of the angle calibration on the distortion correction, the focal point correction, astigmatism correction and the visual field correction.

DESCRIPTION OF THE INVENTION

Figure 1:
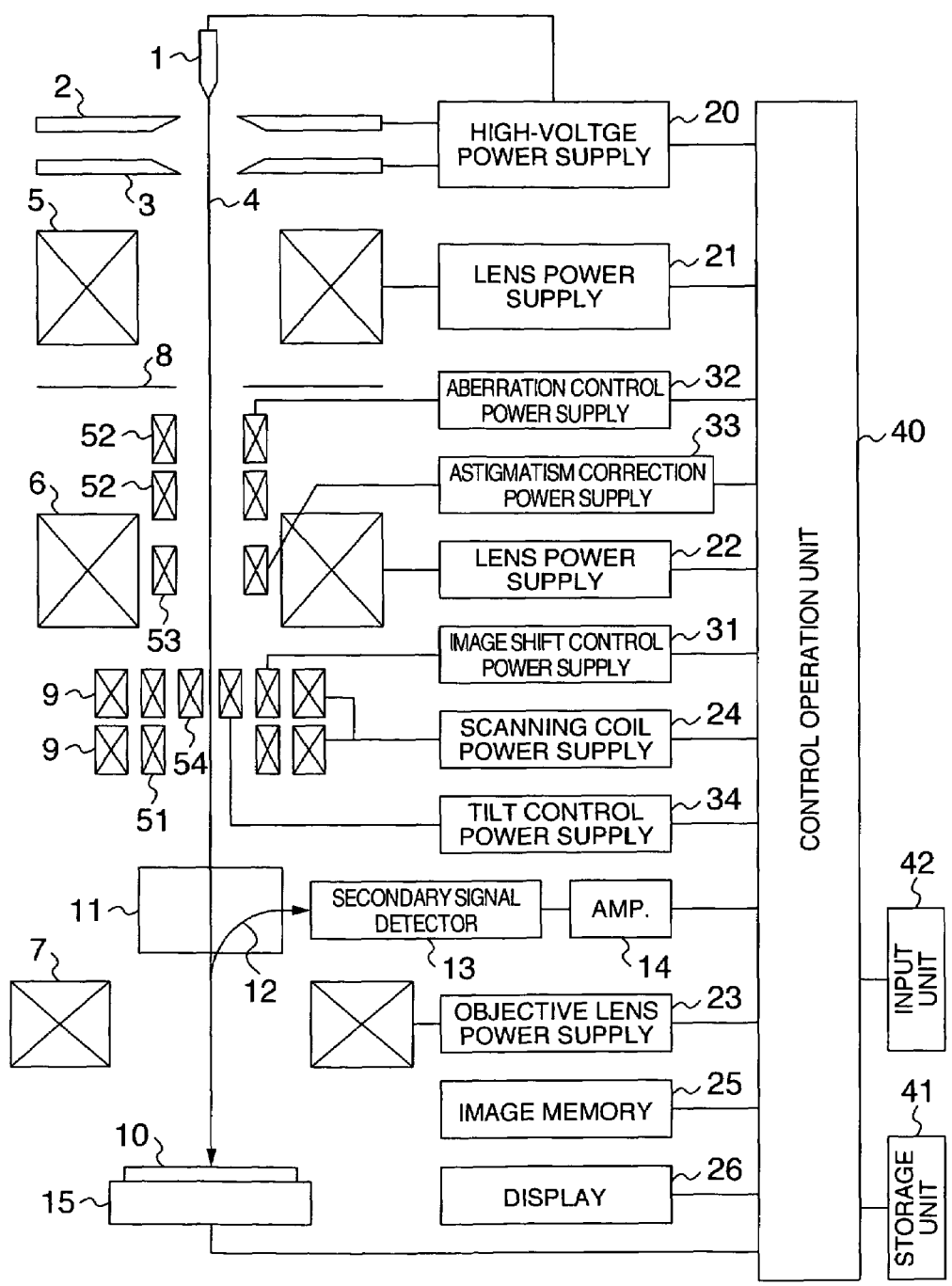
FIG. 1 is a schematic diagram showing a configuration of a scanning electron microscope as an example of the invention.

FIG. 1 is a diagram showing a configuration of a scanning electron microscope according to an embodiment of the invention. Between a negative electrode 1 and a first positive electrode 2, a voltage is applied by a high-voltage control power supply 20 controlled by a control operation unit 40 thereby to extract a predetermined emission current from the negative electrode 1. Between the negative electrode 1 and a second positive electrode 3, on the other hand, an acceleration voltage is applied by the high-voltage control power supply 20 controlled by the control operation unit 40, and therefore the primary electron beam 4 released from the negative electrode 1 is accelerated and proceeds to a subsequent lens system. The primary electron beam 4 is focused by a focusing lens 5 controlled by a lens control power supply 21, and after the unrequited portion of the primary electron beam 4 is removed by an aperture plate 8, focused as a micro spot on a sample 10 by a focusing lens 6 controlled by a lens power supply 22 and an objective lens 7 controlled by an objective lens control power supply 23.

The primary electron beam 4 is two-dimensionally scanned on the sample 10 by a scanning coil 9 controlled by a scanning coil control power supply 24. A secondary signal 12 including the secondary electrons generated from the sample 10 by the radiation of the primary electron beam, after proceeding to a point above the objective lens 7, is separated into the primary and secondary electron beams by a crossed field generator 11 for separation of the secondary signal and detected by a secondary signal detector 13 separate from the primary electron beam. The signal detected by the secondary signal detector 13, after being amplified by a signal amplifier 14, transferred to an image memory 25 and displayed as a sample image on an image display unit 26.

A beam tilt deflector 54 is arranged above the objective lens 7, and the position of the primary electron beam 4 incident to the objective lens can be two-dimensionally controlled by the tilt control power supply 34 in such a manner that the object point of the objective lens constitutes a deflection supporting point. The beam tilt deflector 54 can be any of the electromagnetic deflector and the electrostatic deflector which can tilt the beam. An astigmatism correcting coil 53 is arranged between the focusing lens 5 and the objective lens 7 and controlled by an astigmatism correction power supply 33 in accordance with the beam tilt conditions.

A two-stage deflection coil 52 is arranged between the focusing lens 6 and the aperture plate 8. The position of the primary electron beam 4 incident to the focusing lens 6 can be controlled two-dimensionally by an aberration control power supply 32 in such a manner that the object point of the objective lens 6 makes up a deflection supporting point. As an alternative, the aperture plate 8 is an electrically-operated movable aperture, and by setting the aperture position arbitrarily, the position of the primary electron beam 4 entering the focusing lens 6 through the aperture can be controlled two-dimensionally.

An image shift deflector 51 controlled by an image shift control power supply 31 is arranged at the same position as the scanning coil 9, and in addition to the primary electron beam position control signal to set the object point of the objective lens as a deflection supporting point, can apply a control signal capable of two-dimensionally controlling the sample radiation position of the primary electron beam, so that the shift of the radiation point of the primary electron beam 4 can be corrected in accordance with the beam tilt conditions. The beam can be tilted not only by the beam tilt deflector 54, but by any other device such as an image shift deflector 51 capable of two-dimensionally scanning the position of the primary electron beam 4 incident to the objective lens 7.

The sample stage 15 can move the sample 10 at least in two directions X and Y in the plane perpendicular to the primary electron beam. The image recovery conditions such as the scanning rate and the acceleration voltage and he beam tilt conditions such as as the direction and angle of tilt of the primary electron beam can be designated from the input unit 42. The image output and storage in a storage unit 41 can also be designated from an input unit 42.

In the case where the primary electron beam is radiated in tilted form, many items including the tilt angle, the image distortion generated at the time of tilting, defocusing, astigmatism aberration and the visual field deviation are required to be corrected. Especially, the tilt angle accuracy and the image distortion constitute factors adversely affecting the performance extremely in acquiring the desired tilted image. According to the embodiment of the invention described below, the adjustment for the tilt angle correction and the distortion correction at the time of tilting the beam is efficiently conducted thereby to improve the correction accuracy.

Figure 2:
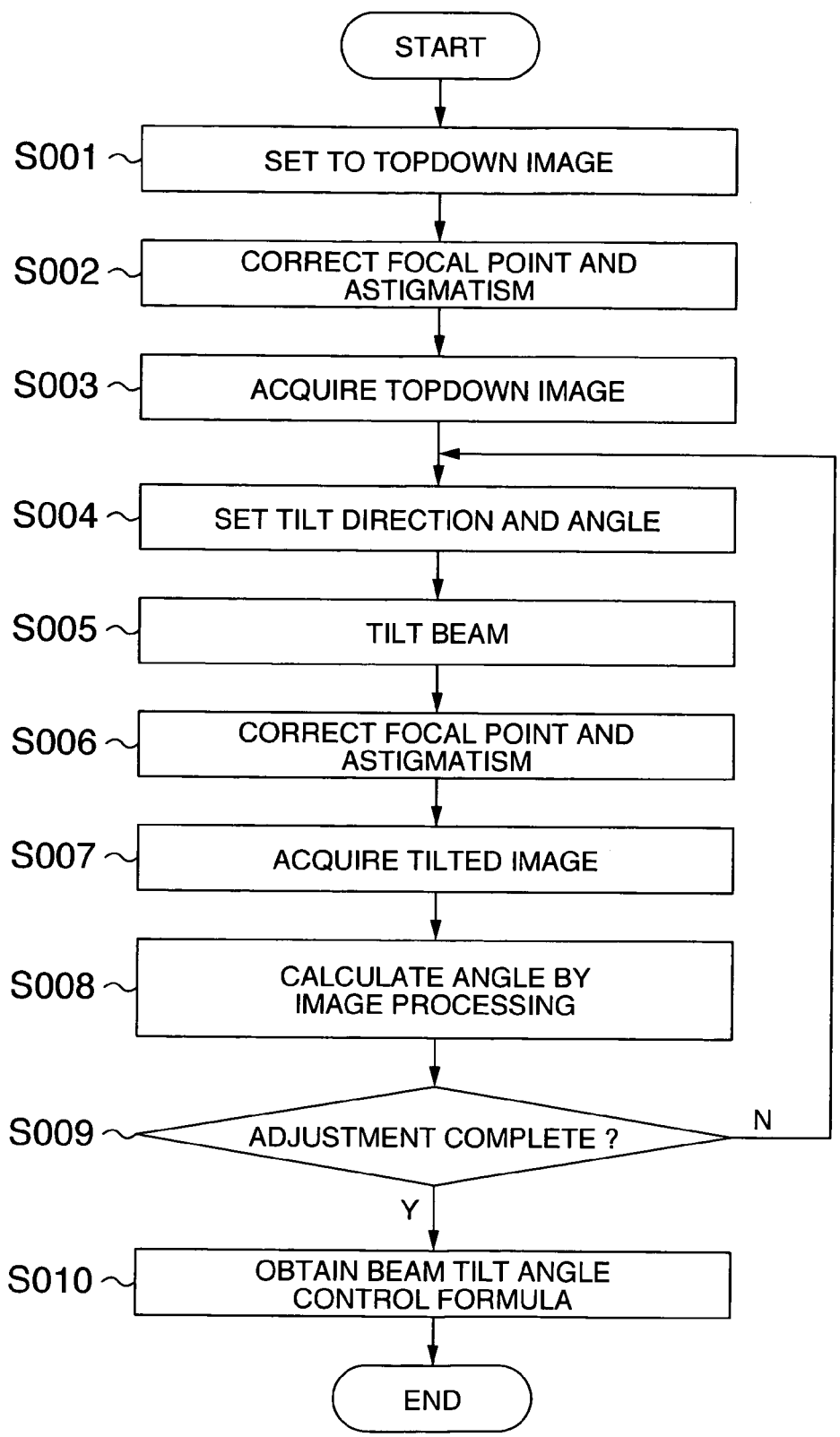
FIG. 2 is a flowchart for explaining the tilt angle adjustment method at the time of tilting an electron beam.

FIG. 2 is a flowchart for the tilt angle adjustment to tilt the electron beam at an angle set by the operator using a pyramidal or the like specified sample. The pyramid may be either concave or convex as predetermined. Using the pyramidal sample, an image before tilt, i.e. a topdown image and an image after tilt, i.e. a tilted image are acquired, and the actual tilt angle of the electron beam can be estimated by image processing. A method of acquiring an equation representing the relation between the current amount or the voltage amount and the angle set in the beam tilt deflector 54 using a pyramidal sample is explained in detail below. Nevertheless, this embodiment is not limited to the pyramidal sample but a sample in any shape of which the tilt angle can be estimated by image processing can be employed.

First, the focal point and the astigmatism are corrected for a topdown image with the beam not tilted (steps S001 to S002), after which the topdown image is acquired and stored in the storage unit 41 (step S003). Next, an appropriate amount is set in the tilt control power supply 34, and the beam is tilted by the beam tilt deflector 54 (steps S004 to S005). After correcting the focal point and the astigmatism at the time of tilting the beam (step S006), a tilted image is acquired and stored in the storage unit 41 (step S007). The edges of the ridge portions of the pyramid are detected by image processing of the two stored images, and the tilt angle is estimated by comparing the geometric shapes formed of the detected edges (step S008). This operation (steps S004 to S008) is repeated a required number of times for each direction (step S009), after which an equation representing the approximate relation between the acquired set amount of the beam tilt deflector 54 and the angle is obtained and defined as a beam tilt angle control formula (step S010). Also in the case where the direction of tilt is changed, an equation representing the relation between the beam deflection amount and the angle for a predetermined direction can be obtained. By conducting the adjustments described above, the beam tilt deflector 54 can be set to a setting amount corresponding to a predetermined setting angle.

According to this embodiment, the devices used for acquiring the relation between the deflection amount and the tilt angle are not limited to the electron beam tilt deflector, but any devices having the function to control the beam tilt can be employed. In the scanning electron microscope with the aperture plate 8 to realize the beam tilt by moving aperture by controlling the track of the primary electron beam 4 in accordance with the aperture position, for example, an approximate equation indicating the relation between the amount of aperture movement and the angle is obtained as an angle control formula.

According to this embodiment, the process described above makes it possible to acquire the tilt angle control formula automatically. In the process, the focal point and the astigmatism can be corrected (steps S002, S006) automatically by presetting a value acquired or estimated in advance or by use of the automatic focal point correcting function and the automatic astigmatism correcting function. In the process, the rough adjustment preset as a condition preceding to the automatic focal point correcting function and the automatic astigmatism correcting function can be carried out by setting the correction amount acquired in advance in topdown state or by setting the correction amount calculated for the set angle to acquire the correction amount with respect to the angle.

The automatic focal point correcting function and the automatic astigmatism correcting function adjust the current amount supplied to the objective lens 7 and the astigmatism correcting coil 53 for adjusting the focal point while at the same time determining the optimum correction amount by image processing. By carrying out the rough correction at the time of tilting the beam, therefore, the variations of the current for the automatic focal point correcting function and the automatic astigmatism correcting function can be suppressed, thereby making possible quick and highly accurate correction.

In the case where the area on the sample scanned by the electron beam changes depending on the beam tilt and an image is shifted, the visual field can be corrected automatically by moving the sample stage 15 by the amount of the visual field shift acquired in advance or by the estimated amount of visual field shift or by controlling the beam radiation position by the image shift deflector. The visual field can be corrected in such a manner that after acquiring the topdown image and the tilted image, the image processing is carried out for pattern matching, and the amount of visual field shift is calculated from the position change on the image. Using this value as the distance covered by the image, the correction is carried out by moving the stage or by the image shift deflector.

FIG. 3 is a flowchart for explaining the adjustment process for correcting the image distortion caused during the beam tilting using a pyramidal sample or the like. First, the focal point and the astigmatism are corrected for an image not tilted, i.e. a topdown image, after which the topdown image is acquired and stored in the storage unit 41 (steps S011 to S013).

Next, the direction and angle of tilt for correcting the distortion are selected (step S014). After tilting the electron beam in the direction and at the angle thus selected (step S015), the focal point and the astigmatism are corrected (step S016), and an image after tilt, i.e. a tilted image is acquired and stored in the storage unit 41 (step S017). In the process, the visual field may be shifted depending on the beam tilt. By moving the sample stage 15 or by deflecting the electron beam by the image shift deflector 51 and moving the electron beam radiation area, however, the visual field is corrected.

Next, the amount of distortion is calculated by image processing using two images in store (step S018). As shown in FIG. 4A, in this case, the secondary electron image obtained by radiating the electron beam 402 perpendicular to the concave pyramidal sample 401 and scanning the electron beam on the sample is a topdown image 403 (FIG. 4B). In the case where the electron beam 404 tilted as shown in FIG. 4G can be scanned without distorting the scanning area, on the other hand, a tilted image 405 (FIG. 4D) can be obtained. In the case where the electron beam is tilted, however, as shown in FIG. 4E, the electron beam scanning area is distorted by the rotation of the distortion aberration. As a result, the image of a square sample is distorted into a parallelogram having the angles 407, 408 to the horizontal and vertical directions on the screen. Also, as indicated by the scanning width 409, 410 in FIG. 4F, the width of area on the sample scanned by the electron beam is changed and therefore the image may be distorted into a rectangle as shown in FIG. 4F. The pyramidal sample is symmetric in both horizontally and vertically. Thus, the rotation value and the aspect ratio to determine the distortion amount can be calculated by acquiring the topdown image and the tilted image, detecting the edges of the ridges of the pyramid by image processing and comparing two images with each other. In this way, the distortion amount can be easily measured.

Next, the process of steps S014 to S018 is repeated as many times as required for each tilt direction (step S019), after which the correction factor is obtained for the distortion correction amount for the tilt angle of the electron beam (step S020).

According to this embodiment, a means for controlling the electron beam scanning area is employed to reflect the correction value acquired at step S020 and correct the distortion generated at the time of tilting the beam. The width of the scanning area and the rotation amount equivalent to the distortion correction value against the set tilt angle are calculated by the control operation unit 40, and a signal is applied to the scanning coil control power supply 24. Thus, a predetermined current is supplied to the scanning coil 9 thereby to correct the distortion.

With the process described above, the adjustment for distortion correction at the time of tilting the beam can be automated. A predicted value for correction of the focal point and the astigmatism is stored in advance, and the correction can be made by setting the value at the time of tilting the beam. As an alternative, the automatic focal point correcting function and the automatic astigmatism correcting function can be used. With regard to the visual field shift caused during the tilting of the electron beam, a predicted visual shift amount is stored, and the actual correction carried out by moving the stage at the time of tilting the beam or by moving the radiation area by the image shift deflector. Alternatively, the topdown image and the tilted image are processed and subjected to the pattern matching, the visual field shift amount is calculated from the image shift, and the correction is carried out with the particular shift as a distance to be covered.

Also, according to this embodiment, the electron beam is tilted by reflecting the acquired correction value, after which the distortion amount is acquired in accordance with the process of steps S011 to S018. As long as the correction is carried out with high accuracy, the distortion amount calculated at step S018 infinitely approaches zero. By using the method according to this embodiment, therefore, the accuracy after adjustment can also be checked. Also, in the case where a threshold is set and the accuracy fails to meet the threshold, the correction value is acquired again and the convergence calculation is executed. In this way, the accuracy of distortion correction can be improved.

Figure 5:
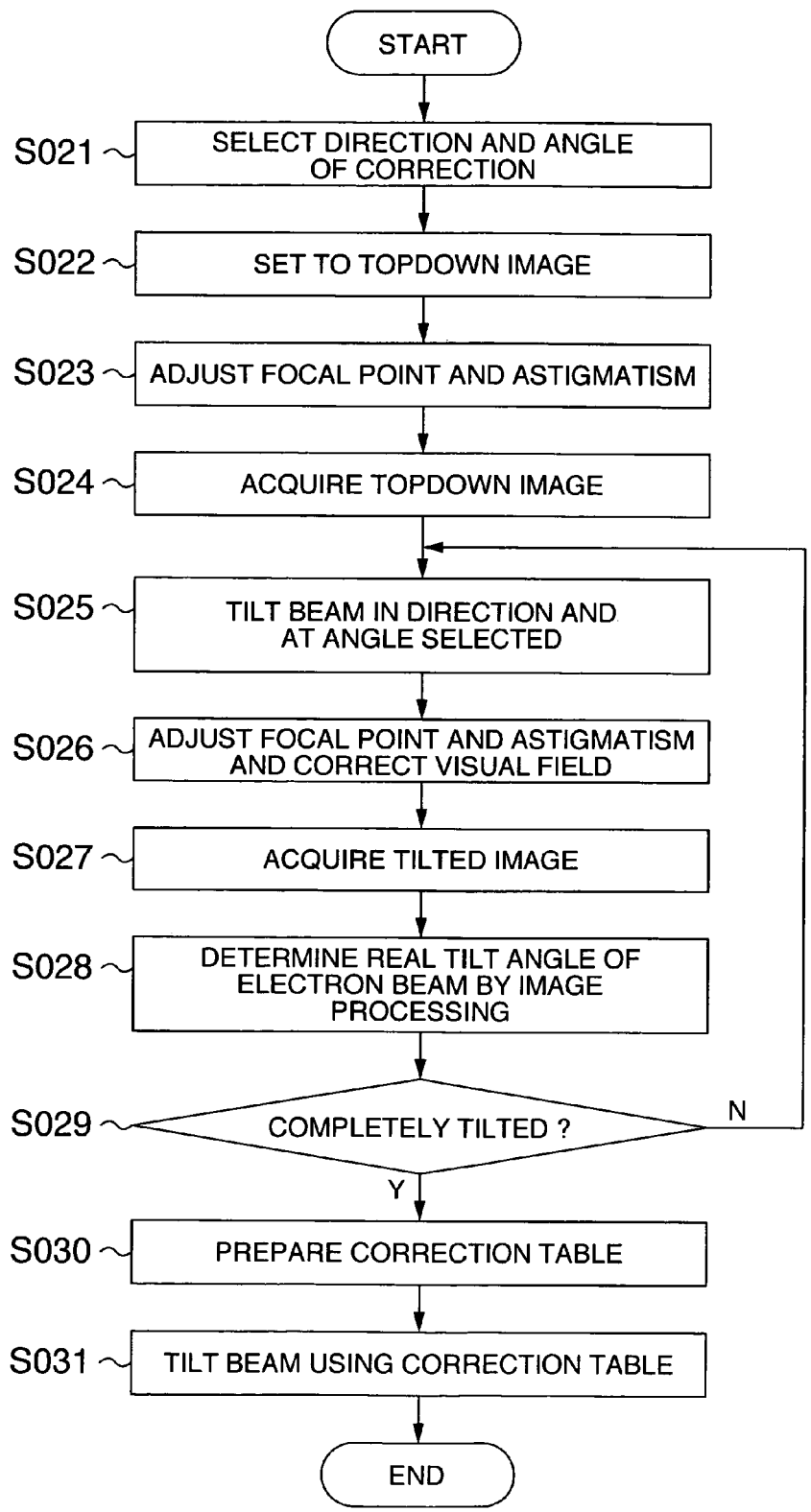
FIG. 5 is a flowchart for explaining an angle calibration method.

FIG. 5 is a flowchart for explaining in detail the correction for improving the accuracy of the tilt angle, i.e. the angle calibration. An embodiment in which the angle calibration is conducted using a pyramidal sample is explained below. Nevertheless, the sample is not limited to a pyramid but any shape of sample can be used as far as the angle can be accurately measured by image processing.

First, the direction and angle of the tilt of the electron beam to be corrected are selected (step S021). The direction and angle of tilt can be either selected by the operator or automatically set by a predetermined process.

Next, a topdown image is set, and after adjusting the focal point and the astigmatism, the topdown image is acquired for a pyramidal sample (steps S022 to S024). Then, with regard to the selected direction and angle, a predetermined current value or voltage value determined from the angle control formula described above is set in the beam tilt deflector thereby to tilt the electron beam (step S025). After that, the focal point adjustment, the astigmatism adjustment and the visual field correction are carried out, and the tilted image is obtained (step S026). The focal point and the astigmatism can also be adjusted by executing the automatic focal point correcting function and the automatic astigmatism correcting function, respectively. In the case of visual field shift generated at the time of tilting the electron beam, a predicted visual field shift amount is stored, and at the time of tilting the electron beam, the correction is carried out by moving the stage or by moving the electron beam radiation area by the correction amount using the image shift deflector. As an alternative, the relation between the tilt angle and the visual field shift amount is acquired in advance, and the correction amount against the set angle is calculated thereby to carry out the correction. As another alternative, the pattern matching is conducted by image processing with the topdown image and the tilted image, the visual field shift amount is calculated from the image shift and the correction is carried out by moving the image by the particular visual field shift amount.

Next, the real tilt angle $\theta_{real}$ is determined by image processing using two images including the topdown image and the tilted image acquired (step S028). As the real tilt angle $\theta_{real}$, the tilt angle component ($\theta_{real\_x}$, $\theta_{real\_y}$) is acquired for X and Y directions of the acquired image.

After acquiring the data for each direction and angle of tilt, a correction table is prepared (steps S029, S030). The correction table shows the direction of the angle component ($\theta real_x$, $\theta real_y$) of the real tilt angle determined by image processing for each direction and angle of tilt. The value input to the correction table may be the very value of the real tilt angle determined by image processing, or any other value such as the error of the real tilt angle with respect to the set angle, i.e. the difference value from which the angle change with respect to the set angle can be determined.

According to this embodiment, after acquiring the correction table as described above, the beam can be tilted by improving the angular accuracy using the acquired correction table (step S031). Once the operator sets the angle $\theta_{set}$, the value of the correction table is read and the calibration angle $\theta_{calib}$ is calculated so that the real tilt angle approaches the set angle, and the angle $\theta_{calib}$ is set as an input value of $\theta_{set}$. In this way, the angle calibration can be carried out. From the value $\theta_{real}$ of the real tilt angle held in the correction table, for example, the ratio of $\theta_{real}$ to the set angle $\theta_{set}$ is acquired, and a new angle is internally set as $\theta_{calib}$ in such a manner that $\theta_{real}$ is equal to $\theta_{set}$ as a tilt angle value. Then, the current or voltage amount corresponding to the ratio is set in the beam tilt deflector, thereby making possible the angle calibration.

According to this embodiment, the method of improving the accuracy of the real tilt angle using the set angle $\theta_{set}$ and $\theta_{real}$ is not limited to the acquisition of the ratio described above. Instead, the error from the set angle, i.e. the difference may be determined, and in the case where the real tilt angle is large, the current amount or the voltage amount for controlling the beam deflection amount corresponding to the angle of the error is applied to the beam tilt deflector. In this way, the tilt angle accuracy can be improved.

Also, according to this embodiment, the tilt angle correction table represents the two-dimensional tilt angle component $\theta_{real\_x}$, $\theta_{real\_y}$, and therefore, in the case where the electron beam is tilted in X direction, for example, the electron beam tilt angle can be corrected with zero tilt angle in Y direction. In the presence of an angular component in Y direction on the correction table at the time of tilting the electron beam in X direction, for example, the current or voltage amount applied to the beam tilt deflector is corrected in such a manner that the angular component in Y direction is zero. This tilt angle correction can realize the electron beam tilt of which the direction can be accurately controlled.

Further, the process of steps S021 to S030 is automated. As described below, the focal point is adjusted by the automatic focal point correcting function, and the astigmatism is corrected by the automatic astigmatism correcting function. Then, the visual field shift caused by the beam tilt is corrected by image recognition before and after the tilt, i.e. by measuring the image shift using the pattern matching. In this way, automation is made possible. In the process, the electron beam may be tilted N times in the same direction at the same angle of tilt, and the real tilt angles acquired are averaged to determine the values on the correction table. By doing so, a highly accurate beam tilt is realized.

Figure 6:
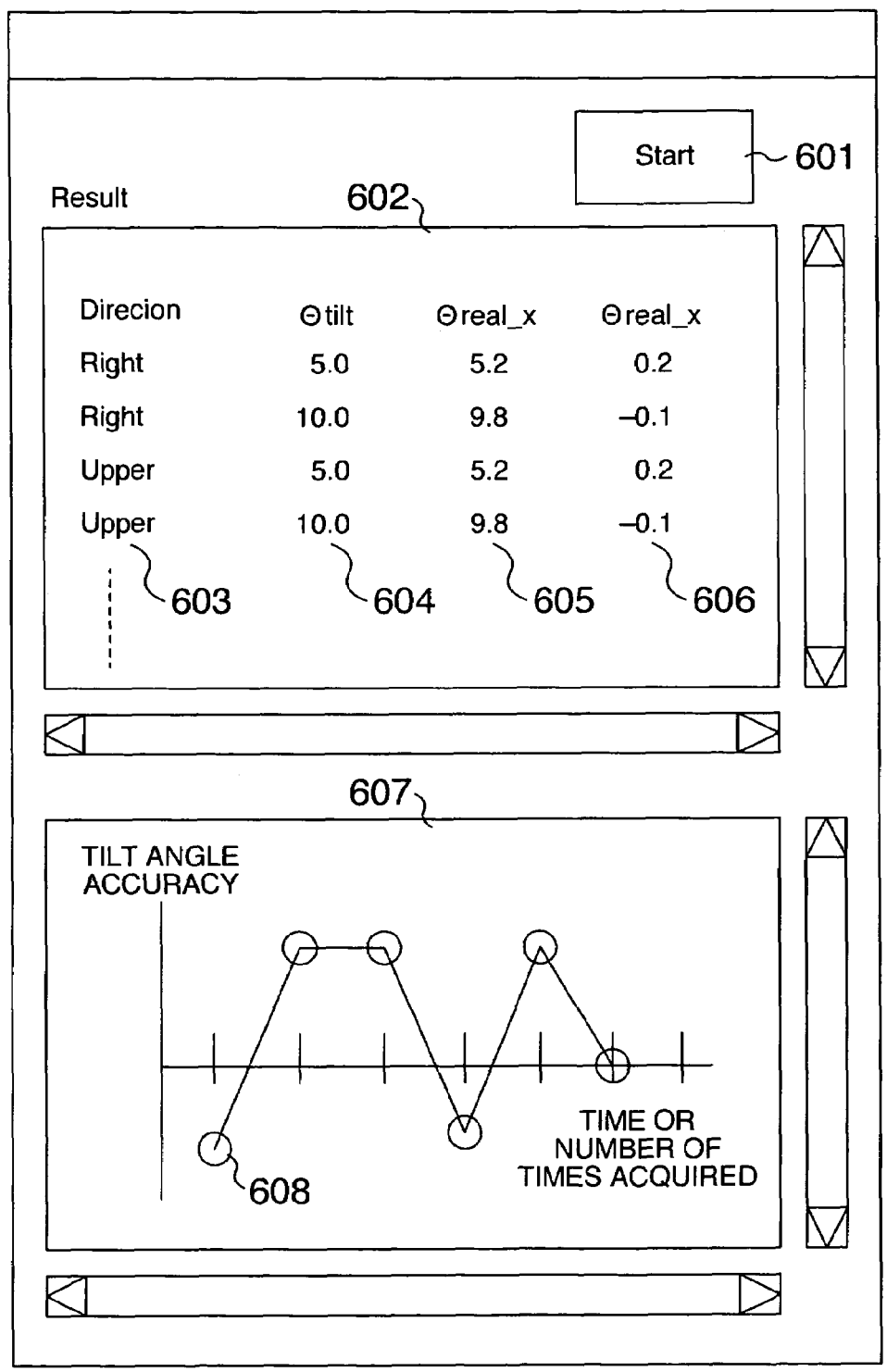
FIG. 6 shows an example of the GUI (graphical user interface) screen to execute the angle calibration.

FIG. 6 shows an example of the GUI screen to carry out the angle calibration described above. The control operation unit 30 has a program to display this GUI screen on the image display unit 26. An angle calibration execution button 601 is operated to carry out the angle calibration in accordance with the process described in FIG. 5. A result display screen 602 displays the result on the correction table prepared by the angle calibration. With the tilt direction 603 and the set angle 604, the X component 605 and the Y component 606 acquired by image processing are displayed.

On a tilt angle accuracy monitor screen 607, the abscissa represents the time or the number of times the angle calibration is carried out, and the ordinate the tilt angle accuracy, so that the correction table value 608 acquired by angle calibration is plotted. In this way, the angular accuracy can be monitored. According to this embodiment, the beam tilt can be easily grasped by visually checking the change in angular accuracy. Further, in the case where the tilt angle accuracy is deteriorated, the beam tilt angle can be adjusted to maintain the angular accuracy. Also, a constant accuracy can be maintained by adjusting the beam tilt angle at regular intervals of time.

In the angle calibration described in the third embodiment, the formula indicating the relation of the correction amount with respect to the angle is acquired in advance for the distortion correction, the focal point correction, the visual field correction and the astigmatism correction required at the time of tilting the beam. Thus, the control operation can be performed by reflecting the result of angle calibration at the time of tilting the electron beam.

FIG. 7 is a flowchart for explaining the method of correction control carried out at the time of tilting the electron beam with or without angle calibration. First, the direction and angle of tilting the beam are selected (step S032). In the case where the angle calibration is carried out, the angle $\theta_{calib}$ calculated by the value on the correction table for angle calibration described in the third embodiment is used as a set angle (step S033), while in the case where the angle calibration is not conducted, on the other hand, the set angle $\theta_{set}$ is used (step S034).

According to this embodiment, whether the angle calibration is carried out or not is determined in accordance with the presence or absence of the calibration value in the correction table for angle calibration described in the third embodiment. Alternatively, the operator may determine arbitrarily.

Next, the correction value is calculated for distortion correction, focal point correction, astigmatism correction or visual field correction, and the correction carried out. In view of the fact that these correction values represent the correction with respect to the angle, the correction value can be calculated in accordance with the value of the set angle regardless of whether the angle calibration is carried out or not. In carrying out the angle calibration, therefore, the correction can be conducted without readjustment for distortion correction, focal point correction, astigmatism correction or visual field correction.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A charged particle beam adjustment apparatus comprising:
    a charged particle source;
    an objective lens for focusing the charged particle beam released from the charged particle source and radiating the focused charged particle beam on a sample;
    a charged particle optical system for scanning the charged particle beam on the sample;
    a detector for detecting the secondary signal particles emitted from the sample by scanning the charged particle beam;
    a tilt deflector for deflecting the charged particle beam out of the axis of the objective lens and tilting the charged particle beam with respect to the optical axis of the objective lens; and a control unit for controlling the charged particle optical system;

wherein the control unit stores a signal amount to be applied to the tilt deflector in accordance with a selected tilt angle of the charged particle beam, compares an image acquired in a state in which the charged particle beam is not tilted by the tilt deflector with an image acquired in a state in which the charged particle beam is tilted by the tilt deflector by the selected tilt angle to determine a real tilt angle of the charged particle beam, and corrects the signal amount on the basis of the determined real tilt angle.

2. A charged particle beam adjustment apparatus according to claim 1, wherein the sample is formed in the shape of pyramid.

3. A charged particle beam adjustment apparatus according to claim 2, wherein the control unit detects edges of the two images of the pyramidal sample and compares the two images having the edges to calculate a rotation value and/or an aspect ratio between the two images.

4. A charged particle beam adjustment apparatus according to claim 1, wherein the control unit generates a signal to be applied to the charged particle optical system on the basis of the measured result.

5. A charged particle beam adjustment apparatus according to claim 4, wherein the control unit stores signals to be applied to the charged particle optical system every tilt angle of the charged particle beam.

6. A charged particle beam adjustment apparatus according to claim 4, wherein the control unit stores signals to be applied to the charged particle optical system every tilt direction of the charged particle beam.

7. A charged particle beam adjustment apparatus according to claim 1, wherein the control unit detects edges in the two images and calculates a rotation value and/or an aspect ratio between the two images.

8. A charged particle beam adjustment apparatus according to claim 1, wherein the control unit controls a scanning signal to be applied to a deflector for scanning the charged particle beam on the basis of the measured result.

9. A charged particle beam adjustment method executed in a charged particle beam apparatus, wherein said apparatus comprises: a charged particle source; an objective lens for focusing the charged particle beam released from the charged particle source and radiating the focused charged particle beam on a sample; a charged particle optical system for scanning the charged particle beam on the sample; a detector for detecting the secondary signal particles emitted from the sample by scanning the charged particle beam; a tilt deflector for deflecting the charged particle beam out of the axis of the objective lens and tilting the charged particle beam with respect to the optical axis of the objective lens; and a control unit for controlling the charged particle optical system; and wherein said method comprises the steps of:

storing a signal amount to be applied to the tilt deflector in accordance with a selected tilt angle of the charged particle beam;

acquiring a first image in a state in which the charged particle beam is not tilted by the tilt deflector;

acquiring a second image in a state in which the charged particle beam is tilted by the tilt deflector by the selected tilt angle;

comparing the first image with the second image to determine an actual tilt angle of the charged particle beam; and correcting the signal amount on the basis of the determined actual tilt angle.

* * * * *